United States Patent [19]

Rathke et al.

[11] Patent Number: 4,656,152
[45] Date of Patent: Apr. 7, 1987

[54] CATALYST FOR PRODUCING LOWER ALCOHOLS

[75] Inventors: Jerome W. Rathke, Bolingbrook; Robert J. Klingler, Woodridge; John J. Heiberger, Glen Ellyn, all of Ill.

[73] Assignee: The United States of America as represented by the United States Department of Energy, Washington, D.C.

[21] Appl. No.: 535,463

[22] Filed: Sep. 26, 1983

[51] Int. Cl.$^4$ .............................................. B01J 31/04
[52] U.S. Cl. ....................................................... 502/170
[58] Field of Search ........................................... 502/170

[56] References Cited

U.S. PATENT DOCUMENTS 2,245,362  6/1941  Pinkney ........................ 502/170 X
4,119,567  10/1978  Bartsch ............................. 502/170

Primary Examiner—W. J. Shine
Attorney, Agent, or Firm—Hugh W. Glenn; Robert J. Fisher; Judson R. Hightower

[57] ABSTRACT

A process and system for the production of the lower alcohols such as methanol, ethanol and propanol involves the reaction of carbon monoxide and water in the presence of a lead salt and an alkali metal formate catalyst combination. The lead salt is present as solid particles such as lead titanate, lead molybdate, lead vanadate, lead zirconate, lead tantalate and lead silicates coated or in slurry within molten alkali metal formate. The reactants, carbon monoxide and steam are provided in gas form at relatively low pressures below 100 atmospheres and at temperatures of 200–400° C. The resulted lower alcohols can be separated into boiling point fractions and recovered from the excess reactants by distillation.

6 Claims, 1 Drawing Figure

CATALYST FOR PRODUCING LOWER ALCOHOLS

CONTRACTUAL ORIGIN OF THE INVENTION

The United States Government has rights in this invention pursuant to Contract No. W-31-109-ENG-38 between the U.S. Department of Energy and Argonne National Laboratory.

BACKGROUND OF THE INVENTION

The present invention relates to the catalytic production of the lower alcohols, methanol and mixtures of methanol with ethanol and propanol, by the reaction of carbon monoxide with liquid water or steam. The process is of particular advantage in that ethanol may be produced directly from carbon monoxide without resorting to a separate and additional process for the conversion of methanol to ethanol. Moreover, carbon monoxide can be provided as a by-product from the steel industry, from the partial oxidation of coal or other carbonaceous material, or from typical coal gasification processes without the necessity of water gas shift processing for increasing hydrogen content.

Previous processes for the production of methanol from carbon monoxide have involved the reaction of carbon monoxide with hydrogen. Copper, zinc and chromium oxides are often selected as catalysts for this process.

In contrast, the reaction of carbon monoxide and water to form methanol is thermodynamically more favorable than the corresponding carbon monoxide and hydrogen reaction. However, prior workers have been unable to realize this advantage at low process pressures by directly reacting carbon monoxide with water in the presence of these known catalysts. Consequently, the elevated process pressures with required thick-walled equipment negates many advantages of the carbon monoxide-water reaction.

The prior processes for the production of methanol from carbon monoxide have produced little ethanol. Subsequent process steps and operations are required for the further conversion of methanol to ethanol. Ethanol is a particularly desirable alcohol as it can be employed not only as a fuel but also as a raw material for the production of ethylene, a chemical used in large quantities in the industrialized countries. In addition, mixtures of methanol with ethanol and propanol are desirable as gasoline extenders. The presence of small amounts of ethanol and propanol prevent phase separation of methanol in the presence of water contamination.

Present processes for the production of methanol most often use raw materials from the steam reforming of methane in natural gases. Coal is not ordinarily used as a raw material as its high sulfur content may poison the catalyst. Also, the ordinary coal gasifier output must be further reacted with water to convert a portion of the carbon monoxide to additional hydrogen. Otherwise, the required two moles of hydrogen per mole of carbon monoxide are not available for methanol production. Catalysts for the water gas shift reaction are also poisoned by sulfur from coal.

SUMMARY OF THE INVENTION

Therefore in view of the above it is an object of the present invention to provide an improved catalyst for the reaction of carbon monoxide with water to produce methanol and other lower alcohols.

It is a further object to provide a process for the production of methanol from carbon monoxide and water in which a relatively inexpensive catalyst permits the reaction at low pressures.

It is also an object to provide a process for the production of methanol in which ethanol is also directly produced.

It is another object to provide a process for the production of mixtures of methanol with ethanol and propanol from the reaction of carbon monoxide and water at moderate pressure with inexpensive catalysts.

It is likewise an object to provide a system for the catalytic production of lower alcohols from the reaction of carbon monoxide and water at moderate pressure with inexpensive catalysts.

In accordance with the present invention, a catalyst combination is provided for the reaction of carb monoxide and water to produce lower alcohols. The catalyst combination includes a lead heteropolyatomic salt in mixture with a metal formate or a precursor to a metal formate salt is a salt of lead and a polyatomic oxygenate.

In more specific aspects the heteropolyatomic lead salt is a polymeric lead salt of lead and a polyatomic anion containing a transition metal oxygenate, which salt exhibits resistance to reduction to lead metal in the presence of carbon monoxide.

A more specific heteropolyatomic salt is selected from the oxygen containing salts, lead titanates, lead molybdates, lead tungstates, lead vanadates, lead zirconates, lead tantalates and lead silicates.

In other specific aspects, particles of the lead heteropolyatomic salt are coated with alkali metal formate or dispersed within molten alkali metal formate.

In other aspects of the present invention, a process is provided for producing a lower alcohol from the reaction of carbon monoxide and water. The process involves passing a gas mixture of carbon monoxide and steam into contact with a catalyst combination including a lead salt, that is essentially not reduced to lead metal by carbon monoxide, and a co-catalyst comprising metal formates or precursors to metal formates under the reaction conditions. These catalysts promote the reaction of carbon monoxide and water to form a lower alcohol typically including methanol, often ethanol and in some instances propanol.

In more specific aspects of the invention, the lead salt is formed of lead and a polyatomic anion comprising a transition metal oxygenate.

In other more specific aspects the lead salt can be selected from lead titanates, lead molybdates, lead tungstates, lead vanadates, lead zirconates, lead tantalates and lead silicates.

In other specific aspects of the invention the gas mixture of carbon monoxide and steam is at a pressure of 1–200 atmospheres and a temperature of 200°–400° C. when it contacts the catalysts combination. More specifically, the pressure of the reaction conditions is 10 to 100 atmospheres and the temperature is 350°–375° C.

In one other specific aspect of the invention the steam in the gas mixture is about 1–60 volume percent but the carbon monoxide is provided in excess of a stoichiometric ratio of 3 to 2 volume parts in respect to steam.

In further specific aspects of the process, carbon monoxide is provided by a partial oxidation of carbonaceous material with a dry gas including less than stoichiometric oxygen content in accordance with the reaction:

$$C + \tfrac{1}{2}O_2 \rightarrow CO.$$

The invention also contemplates a method of producing methanol and ethanol by reacting carbonaceous material with a dry gas containing oxygen to form carbon monoxide substantially in excess of any carbon dioxide and hydrogen produced. Sufficient steam is added to the gas to comprise 0.1 to 0.65 volume fraction of the carbon monoxide and the gas is at a pressure of 10 to 100 atmospheres at a temperature of 200°–400° C. is passed into contact with a catalyst including solid particles of lead titanate coated with molten alkali metal formate to react the gases and form both ethanol and methanol.

The invention further contemplates a catalytic system for the production of lower alcohols including methanol. The system comprises a catalyst including particles of a lead salt, having an oxygenated anion, in contact with a liquid phase containing a co-catalyst including a metal formate or a precursor of a metal formate. Process equipment means are provided for contacting the catalyst and co-catalyst with a gas mixture containing carbon monoxide and steam to form a gas phase containing the lower alcohol. Fractionation means permit recovering the lower alcohol from the gas phase mixture.

In other specific aspects of the invention, the particles of the lead salt have coatings of molten alkali metal formate and are assembled into a porous bed in communication with means provided for contact with the gas mixture.

In other more specific aspects the catalyst is provided as a slurry of solid particles of the lead salt in molten alkali metal formate.

In one other aspect of the invention the catalyst is provided as particles of the lead salt in slurry within a solution having an alkali metal formate solute in a polyamine solvent.

BRIEF DESCRIPTION OF THE DRAWINGS

The present invention is illustrated in the accompanying figure, which is a diagrammatic flow diagram of a process for the production of lower alcohols.

DETAILED DESCRIPTION OF THE PREFERRED EMBODIMENT

Figure 1:
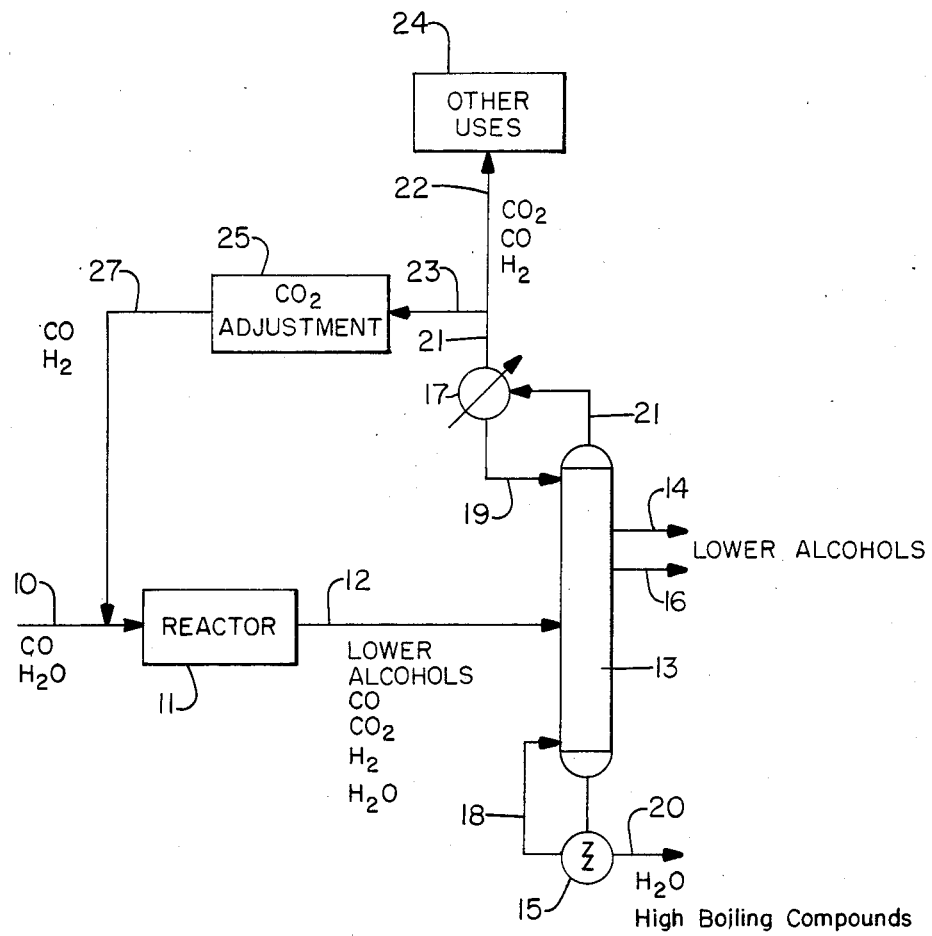

The method and system of the present invention involves the reaction of carbon monoxide with water to form methanol and carbon dioxide in accordance with the following reaction $$3CO + 2H_2O \rightarrow CH_3OH + 2CO_2 \quad (1)$$

This reaction offers a substantial thermodynamic advantage over the reaction of prior processes in which carbon monoxide is reacted with hydrogen to form methanol.

$$CO + 2H_2 \rightarrow CH_3OH \quad (2)$$

The reaction of carbon monoxide with water is accompanied by a change in free energy of formation at 298° K. of −19.5 KCAL as compared with only −5.9 KCAL in the case of the reaction with hydrogen. Accordingly, applicants process and system can provide for methanol production at milder conditions than that required in prior processes.

As the process of applicants' method of ethanol production requires little if any hydrogen gas, the carbon monoxide may be provided merely by the partial oxidation of carbonaceous material such as coal. The amount of oxygen or air can be limited to avoid production of carbon dioxide. This partial oxidation of carbon as in coal or other carbonaceous material enjoys a further thermodynamic advantage in respect to change in free energy over the customary gasification reaction for carbonaceous material. Ordinarily coal is gasified by reaction with water to form carbon monoxide and hydrogen. However, only one mole hydrogen is provided for each mole of carbon monoxide. Thus, further processing is required by the water gas shift reaction to provide sufficient hydrogen for reaction with carbon monoxide.

Applicants process and method involves a completely different reaction system than the mere combination of water gas shift and the reaction of carbon monoxide with hydrogen to form methanol. The following two reactions are proposed in explanation of applicants method for the production of methanol.

$$4O_2CH^- \rightarrow CH_3OH + CO + 2CO_3^{-2} \quad (3)$$

$$CO_3^{-2} + H_2O + 2CO \rightarrow 2O_2CH^- + CO_2 \quad (4)$$

The net catalytic reaction obtained by adding reactions (3) and (4) is that given above in reaction (1) for combining carbon monoxide and water to produce methanol.

It is of considerable importance that a suitable catalyst be found for these reactions. Many known catalysts are inappropriate as they are inconsistant with both the methanol production reaction and the renewal of the formate ion. For example, oxides of lead such as $PbO_2$ are reduced in the carbon monoxide environment to form lead metal to impair its catalytic activity. Other catalysts such as copper and zinc oxides or metals are poisoned by any sulfur containing gases that may accompany carbon monoxide produced in the gasification or partial oxidation of ordinary coals.

The inventors have found a new catalyst combination that permits the production of methanol and in some instances direct production of ethanol and propanol from the reaction of carbon monoxide and water. The catalyst includes solid particles of a lead salt containing a polyatomic anion in contact with a metal formate. Although many lead salts may catalyze the conversion of formate ion to methanol, the inventors have found that the combination of lead with certain polyatomic anions provides lead in a combined form that is essentially not reduced by carbon monoxide under the conditions of the present process. For purposes of this application, the term "lead heteropolyatomic salt" refers to the combination of lead with a polyatomic anion such as the oxygenates of the transition metals and of silicon.

The lead heteropolyatomic salts that have been found suitable for the inventors' process include anions of oxidized transition metals. For example, the lead titanates, lead molybdates, lead tungstates, lead vanadates, lead zirconates and lead tantalates are contemplated. In addition to these salts involving transition metals, the lead silicates also have catalytic activity in the present method. Applicants also have found that the lead titanate, $PbTiO_3$ is effective for the direct conversion of carbonaceous material to ethanol and propanol in addition to methanol. Other particular compositions are $PbMoO_4$, $PbV_2O_6$, $PbZrO_3$, $PbWO_4$ and $PbTaO_3$. Each of these heteropolyatomic lead salts are generally in the form of large molecular weight polymers.

Lead heteropolyatomic salts are commercially available generally as paint pigments as opposed to catalytic compositions.

Although not tried, it is contemplated that other group 4A metals such as Ge or Sn may be used in place of lead in combination with formate as catalyst for the reaction of this invention.

A large number of metal formates may be suitable for use in combination with the heteropolyatomic lead salt in the present catalytic system. Potential metal formates include the alkaline earth metal formates and the transition metal formates. However, the high solubility and low melting points of the alkali metal formates make them the selection of choice. Through use of mixtures of lithium formates, potassium formates, and sodium formates, melting points lower than any of the individual alkali metal formates can be obtained. For example the eutectic composition of 25% lithium formate and 75% potassium formate has a melting point of only 118° C.

The metal formates selected may be provided as such or as a suitable precursor to the metal formates. For example, metal carbonates convert to formates as shown in reaction 4 above.

It is therefore clear that the present process and system involve a catalyst combination including a primary catalyst of a lead heteropolyatomic salt and a co-catalyst of a metal formate or a precursor to a metal formate. The catalyst and co-catalyst can be combined in a number of varied forms such that both will have access to the reactants. The primary catalyst of lead heteropolyatomic salt is preferably in the form of solid particles while the formate is preferably in molten state or as a solute within a liquid solvent. For example, a catalyst bed comprising solid particles of lead heteropolyatomic salt coated with molten metal formate can be selected. Such a bed can easily be prepared merely by blending the molten metal formate into the particulate lead salt particles. In one other catalyst form, the particles of lead salt can be dispersed in molten metal formate to form a slurry.

The inventors have found one other form for the catalytic system by dissolving metal formate, particularly alkali metal formate into a liquid polyamine. Amines such as pentamethyldiethylenetriamine and heptamethyltetraethylenepentamine have been employed as solute. In addition, tetraethylenepentamine has been attempted with somewhat less effective results.

Although all of the above forms of the presently described combination catalysts are effective in the production of methanol and in some instances ethanol and propanol, the inventors have found that the bed of lead salt particles coated with alkali metal formate is a preferred mode. It should further be recognized that the bed of particles can be employed as a catalyst either as a fixed bed or as a fluidized bed within an appropriate reactor vessel.

In one manner of carrying out the method of the present invention the catalyst combination as described is contained within a reactor vessel and the reactant gases of carbon monoxide and steam are passed into contact with the catalyst. The reactor can be simply a single chamber for a fixed bed or fluidized bed of catalyst or may be a tubular reactor having a plurality of tubes filled or partially filled with the catalyst combination.

The carbon monoxide and steam typically are provided at about 1 to 60 volume percent steam. However, since an excess of water or steam impairs the selectivity of alcohols over hydrogen production it is preferred that the carbon monoxide be provided in stoichiometric excess to that of steam. A particularly effective gas combination is about 70 volume percent carbon monoxide and 30 volume percent steam. The gases are provided at a temperature of about 200°–400° C. and more particularly at about 350°–375° C. Temperatures above 400° C. in many instances causes the catalyst to become unstable and temperatures much below 200° C. renders the reaction unacceptably slow. Following contact with the catalyst resulting in the formation of the lower alcohols, the resulting gas phase mixture can be condensed and separated by fractionation to recover the alcohol products. Excess reactants can be recycled to the catalyst for additional reaction.

Turning now to the drawing, one illustration of a lower alcohol production system is shown.

A gas mixture 10 of carbon monoxide in steam is passed into a reactor vessel 11 where the gas mixture comes in contact with the combination catalyst described herein. The reactor discharge in the gas phase can include excess reactants of steam and carbon monoxide as well as reaction products of methanol, ethanol, propanol and carbon dioxide. In addition some hydrogen gas may be formed as a result of minor water gas shift reaction. The gas phase product 12 is condensed and separated within a fractionating column 13 that includes a condenser 17 with flux liquid 19 and a bottom reboiler 15 with return vapor 18. The various fractionated streams can be withdrawn in accordance with their boiling points. Water and other high boiling compounds are taken at the lower portion of the column at 20. The product fractions 14 and 16 containing the lower alcohols are shown at higher levels in the fractionating column and the very low boiling or non-condensible gases at 21. In order to prevent a build up of undesirable gases, such as carbon dioxide or nitrogen, a fraction 22 may be vented for other uses 24.

The carbon dioxide produced in the formation of methanol can be adjusted by a number of techniques illustrated diagrammatically at 25. Some hydrogen may already be in the process or may be added to reduce the carbon dioxide to carbon monoxide with the formation with water. In addition the carbon dioxide adjustment at 25 may involve carbon reduction to carbon monoxide in the presence of a catalyst such as iron. Such reduction may also occur within reactor 11. Carbon dioxide also may be removed by conventional amine based scrubbers. The remaining excess reactants illustrated at 27 can be recycled to feed stream 10 and to reactor 11.

The following examples are presented merely to illustrate the present invention and not to limit the scope beyond that defined in the claims.

EXAMPLES I–VII (Molten Alkali Metal Formate Slurry)

The molten alkali metal formate salt of the composition indicated in columns 4–6 of Table I below was dried at 300° C. for 12 hours. The heteropolyatomic lead salt catalyst indicated in columns 2–3 of Table I was added and stirred to form a suspension. The reaction was carried out at one atmosphere pressure by adding water with the aid of a precision syringe pump and carbon monoxide directly to the stirred salt suspension at the rates indicated in columns 3 and 4 of Table II. Liquid products were condensed from the exit gas stream as indicated in columns 5-7 of Table II while the complete composition of the vent gas was monitored as indicated in Table III through a septa port.

EXAMPLE VIII (Polyamine Solvent Slurry)

A mixture of 30 grams of lead titanate and 18 grams of lithium formate was suspended in 45 grams of pentamethyldiethylenetriamine solvent with mechanical agitation. The results are as indicated in Tables II and III.

EXAMPLE IX (Continuous Operation in a Tube Reactor)

An intimate mixture of 50 grams lead titanate and 14 grams of potassium formate was placed into a glass lined stainless steel tube with an internal volume of 80 CC. Carbon monoxide at 11 grams/hr and water at 300 μ/hr were passed up through the tube at a pressure of 34 atmospheres, guage, and a temperature of 350° C. After approximately 24 hours the composition of the exit gas had reached a steadystate yielding methanol (1.2 μ/hr), ethanol (0.4 μ/hr) and propanol (0.07 μ/hr).

TABLE I

| INITIAL MOLTEN SALT COMPOSITION | | | | |
|---|---|---|---|---|
| | Catalyst | | Formate Salt | |
| Type | Amount (g) | $HCO_2Li$ (g) | $HCO_2K$ (g) | $HCO_2Na$ (g) |
| EX I    | $PbTiO_3$ | 30  | 13 | 63  | 0   |
| EX II   | $PbTiO_3$ | 30  | 39 | 189 | 0   |
| EX III  | $PbTiO_3$ | 30  | 39 | 189 | 0   |
| EX IV   | $PbMoO_4$ | 205 | 39 | 114 | 100 |
| EX V    | $PbV_2O_6$ | 30 | 53 | 189 | 0   |
| EX VI   | $PbV_2O_6$ | 30 | 53 | 189 | 0   |
| EX VII  | $PBWO_4$  | 30  | 53 | 189 | 0   |

TABLE II

| AVERAGE PRODUCTION RATES - 24 HRS | | | | | |
|---|---|---|---|---|---|
| | Temp. | CO (ml/min) | $H_2O$ (μl/hr) | MeOH (μl/hr) | EtOH (μl/hr) | PrOH (μl/hr) |
| EX I      | 250 | 25 | 19 | 2.8  | 1.0 | 0   |
| EX II     | 315 | 35 | 40 | 19   | 7.8 | 2.1 |
| EX III    | 350 | 40 | 40 | 28   | 16  | 3.5 |
| EX IV[a]  | 250 | 15 | 57 | 334  | 0   | 0   |
| EX V[b]   | 180 | 15 | 9  | 7.7  | 0   | 0   |

TABLE II-continued

| AVERAGE PRODUCTION RATES - 24 HRS | | | | | |
|---|---|---|---|---|---|
| | Temp. | CO (ml/min) | $H_2O$ (μl/hr) | MeOH (μl/hr) | EtOH (μl/hr) | PrOH (μl/hr) |
| EX VI[c]  | 225 | 15 | 84 | 23.  | 0   | 0 |
| EX VII    | 180 | 25 | 84 | 20   | 0   | 0 |
| EX VIII   | 170 | 9  | 8  | 0.6  | 0.2 | 0 |

[a] also yields $HCO_2CH_3$ at 133 μl/hr
[b] also yields acetone at 6.3 μl/hr
[c] also yields acetone at 0.5 μl/hr

TABLE III

| VENT GAS ANALYSES AFTER 24 HRS | | | | | |
|---|---|---|---|---|---|
| | $CH_3OH$ (%) | $H_2O$ (%) | $H_2$ (%) | CO (%) | $CO_2$ (%) |
| EX II   | 3.9 | 24  | 1.3  | 71 | .07 |
| EX III  | 2.7 | 8.4 | 16.  | 73 | .07 |
| EX IV   | 15. | 7.9 | 23.  | 37 | 17  |
| EX V    | 1.5 | 12. | 14.  | 72 | 1.3 |
| EX VIII | .07 | 2.1 | 0.1  | 98 | .05 |

Although the present invention is described in terms of specific embodiments, it will be appreciated by one skilled in the art that various modifications can be made within the scope of the following claims.

The embodiments of this invention in which an exclusive property or privilege is claimed are defined as follows:

1. A catalyst combination for the reaction of carbon monoxide and water to produce lower alcohols, said catalyst combination comprising a lead heteropolyatomic salt in mixture with a metal formate or a precursor to a metal formate said heteropolyatomic salt is a salt of lead and a polyatomic oxygenate.

2. The catalyst combination of claim 1 wherein said heteropolyatomic lead salt is a polymeric lead salt of lead and a polyatomic anion containing a transition metal oxygenate, said lead salt exhibiting resistance to reduction to lead metal by carbon monoxide.

3. The catalyst combination of claim 1 wherein said heteropolyatomic lead salt is selected from the group of oxygen containing salts consisting of the lead titanates, lead molybdates, lead tungstates, lead vanadates, lead zirconates, lead tantalates and lead silicates.

4. The catalyst combination of claim 1 wherein particles of said lead heteropolyatomic salt are coated with molten alkali metal formate.

5. The catalyst combination of claim 1 wherein said lead heteropolyatomic salt is dispersed within molten alkali metal formate.

6. The catalyst combination of claim 1 comprising particles of lead heteropolyatomic salt in slurry within a solution having an alkali metal formate solute in a polyamine solvent selected from the group consisting of tetraethylenepentamine, pentamethyldiethylenetriamine, and heptamethyltetraethylenepentamine.

* * * * *